United States Patent [19]

Waerve

[11] 4,326,131
[45] Apr. 20, 1982

[54] MOBILE X-RAY APPARATUS

[75] Inventor: Hans Waerve, Sollentuna, Sweden

[73] Assignee: Siemens Aktiengesellschaft, Berlin & Munich, Fed. Rep. of Germany

[21] Appl. No.: 112,905

[22] Filed: Jan. 17, 1980

Related U.S. Application Data

[63] Continuation of Ser. No. 940,376, Sep. 7, 1978, abandoned.

[30] Foreign Application Priority Data

Oct. 3, 1977 [DE]  Fed. Rep. of Germany ... 7730503[U]

[51] Int. Cl.³ .............................................. G03B 41/16
[52] U.S. Cl. ................................................. 250/523
[58] Field of Search ........................ 250/522, 523, 525

[56] References Cited

U.S. PATENT DOCUMENTS 3,790,805  2/1974  Foderaro ............................ 250/523
3,801,790  4/1974  Gotzl ................................. 250/523

Primary Examiner—Craig E. Church
Attorney, Agent, or Firm—Hill, Van Santen, Steadman, Chiara & Simpson

[57] ABSTRACT

The disclosure relates to a mobile x-ray apparatus comprising a support whose one end is mounted onto a carriage, whose other end bears an x-ray tube, and which is so constructed that the x-ray tube is freely adjustable in space. The carriage manifests, on its upper side, a stage for accommodating the x-ray tube in a parking position well below eye level of the operator.

3 Claims, 1 Drawing Figure

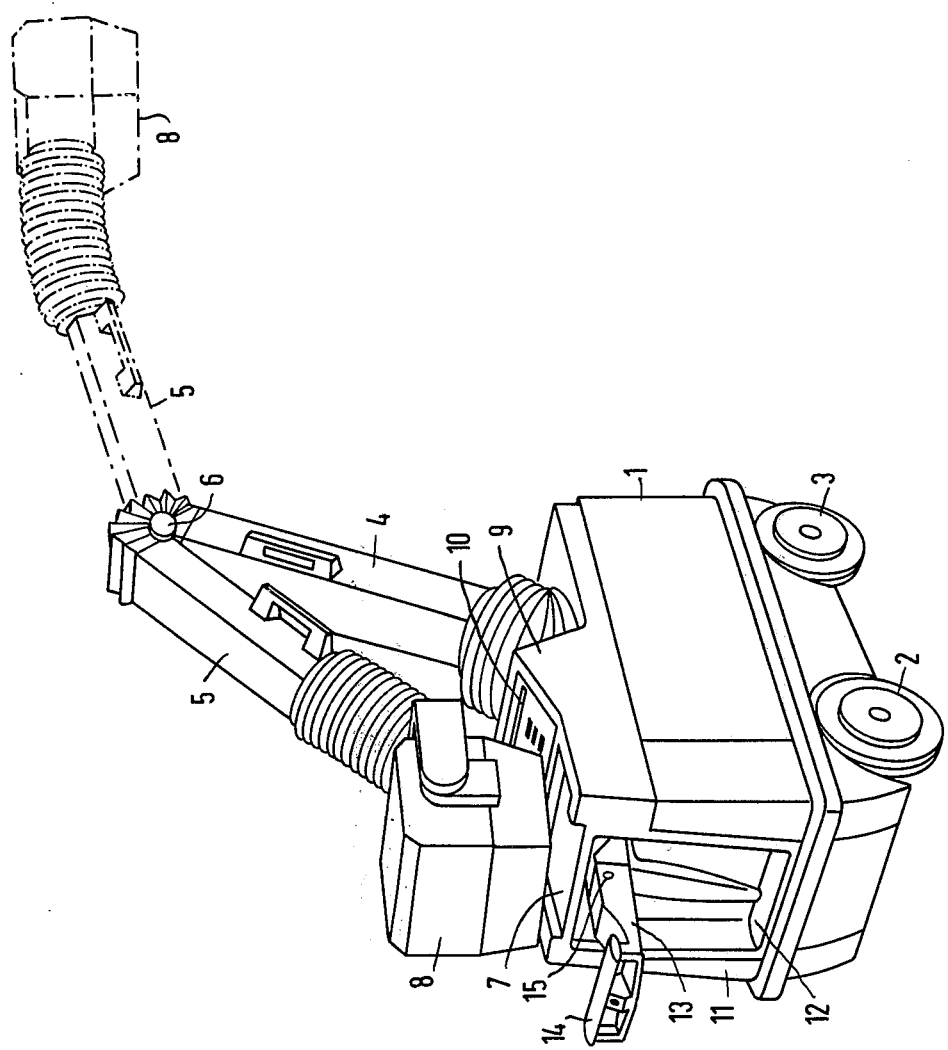

MOBILE X-RAY APPARATUS

This is a continuation of application Ser. No. 940,376, filed Sept. 7, 1978 now abandoned.

BACKGROUND OF THE INVENTION

This invention relates to a mobile x-ray apparatus comprising a stand or support whose one end is mounted onto a carriage, whose other end bears an x-ray tube, and which is constructed in such a manner that the x-ray tube can be freely adjusted in space.

An x-ray apparatus of this type is known from the brochure "Kondiamobil 125" of the Siemens firm. In the case of this apparatus, the stand with the x-ray tube projects upwardly to a great extent during transport, causing an obstruction of view.

SUMMARY OF THE INVENTION

The object underlying the invention consists in producing a mobile x-ray apparatus of the type initially cited wherein the viewing conditions during transport are improved.

This object is achieved in accordance with the invention by virtue of the fact that the carriage manifests at its upper side a stage for the purpose of accommodating the x-ray tube in a parking position. In the case of the inventive x-ray apparatus, the x-ray tube can be pushed downwardly to such an extent prior to transport that the user can see beyond the x-ray tube housing and be provided with a good overview.

A particularly expedient further embodiment of the invention consists in that the upper side of the carriage between the stage and the coupling location of the stand rises obliquely in an upwardly direction and forms a control panel. In this further development, a ready survey and accessibility of the operating elements of the control panel is provided during use of the apparatus.

The invention shall be explained in greater detail in the following on the basis of a sample embodiment illustrated in the accompanying drawing; other objects, features and advantages will be apparent from this detailed disclosure and from the appended claims.

BRIEF DESCRIPTION OF THE DRAWING

The single FIGURE is a perspective view illustrating a mobile x-ray apparatus incorporating features in accordance with an embodiment of the present invention.

DETAILED DESCRIPTION

The FIGURE illustrates a mobile x-ray apparatus comprising a carriage 1 which is provided with four wheels, of which only two wheels 2, 3 are visible. Rear wheel 2 and the opposite, non-visible rear wheel are capable of being steered. On the upper side of the carriage 1 there is arranged a support comprising a pivotally mounted carrier arm 4 which, at its free end, is connected in an articulated fashion to a second carrier arm 5 by means of an axis 6. On the one hand, carrier arm 5 bears, at its free end, by means of a yoke, an x-ray tube assembly including a collimator arranged in a housing 8. There is also disposed in housing 8 the high voltage generator, whereas the switching and control elements are arranged on carriage 1 in and on its housing.

On its upper side, the carriage 1 manifests a stage 9 at which the upper side of carriage 1 rises obliquely in an upward direction and forms an operating or control panel 10 for the purpose of adjusting the photographic parameters. Carriage 1 further manifests at its upper side a stage 7 for accommodating housing 8 in a parking position, which stage 7 provides a recess into which housing 8 fits. On the one end, face 11 of carriage 1, a recess 12 is present in the housing of said carriage, from which recess a steering bar 13 with a handle 14 projects which serves the purpose of steering the motor-driven rear wheels. There is arranged on handle 14 a non-illustrated operating button for the purpose of switching on and off the motor-driven wheels. The steering bar 13 is pivotally mounted about an axis 15 and can be folded into the recess 12.

In order to transport the x-ray apparatus, housing 8 is pushed into the parking position with the housing 8 seated in the recess of stage 7 such that the x-ray tube, the collimator, and the high voltage generator, present in housing 8, are protected against accidental impact. For an x-ray photograph, the housing 8 can be freely adjusted in space as is shown by the position of the carrier arm 5 and housing 8, illustrated by broken lines. Through an equilibration device, the weight of arms 4, 5, and of housing 8 with its components is compensated.

It will be apparent that many modifications and variations may be effected without departing from the scope of the novel concepts and teachings of the present invention.

I claim as my invention:

1. An improved mobile X-ray unit with a wheeled carriage having four sides and a top, a two-part articulated arm connected at a first end to a first end of the top of the cart, a housing, containing an X-ray collimator and high voltage generator, pivotably connected to a second end of the two-part articulated arm, the two-part arm is movable to permit positioning of the housing, a steering bar pivotably attached to a side, at the opposite end of the carriage, the bar extends out from the side of the carriage essentially perpendicular thereto, and is located at a height from the floor so that an operator can use a handle attached to the bar to steer the cart, the improvement comprising:

a recess in the end of the top, adjacent the side to which the steering bar is attached, said recess has a lower essentially horizontal surface substantially corresponding in size to thebottom of the housing, said essentially horizontal surface is bounded by at least two spaced apart essentially vertical sides of a selected height and length joined by a third essentially vertical side, said three sides of said recess are adapted to receive a section of the housing with the bottom of the housing positionable adjacent said essentially horizontal surface when the housing is in a parking position to protect the collimator and high voltage generator from accidental impact while the unit is being moved.

2. The improved mobile X-ray unit according to claim 1 including further:

a control panel located between said recess and the first end of said two-part articulated arm, said control panel is oriented at a selected angle with respect to the horizontal for viewing and accessibility when the unit is in use, a lower edge of said control panel is adjacent said third side of said recess.

3. An improved mobile X-ray unit with a wheeled carriage having four sides and a top, a two-part articulated arm connected at a first end to a first end of the top of the carriage, a housing, containing an X-ray tube, pivotably attached to a second end of the two-part arm, the two-part arm is movable to permit an operator to manually position the housing, the improvement comprising:

a control panel substantially centrally located on the top oriented at a selected angle with respect to the horizontal with a high edge adjacent the first end of the top of the carriage;

a recess in the other end of the top of the carriage, adjacent a lower edge of said control panel, said recess is formed with a lower essentially horizontal surface substantially corresponding in size to the bottom of the housing, said essentially horizontal surface is bounded by two spaced apart essentially vertical sides joined by a third essentially vertical side, said third side is adjacent said lower edge of said control panel, said three sides of said recess are adapted to receive a section of the housing with the bottom of the housing positionable adjacent said essentially horizontal surface when the housing is in a parking position to protect the X-ray tube during transport of the unit and to minimize blocking of an operator's vision during transport of the unit.

* * * * *